United States Patent
Myllyoja et al.

(10) Patent No.: US 11,279,665 B2
(45) Date of Patent: Mar. 22, 2022

(54) PROCESS FOR PRODUCING RENEWABLE PRODUCTS

(71) Applicant: Neste Oyj, Espoo (FI)

(72) Inventors: Jukka Myllyoja, Porvoo (FI); Petro Silvonen, Porvoo (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 17/419,885

(22) PCT Filed: Dec. 17, 2019

(86) PCT No.: PCT/FI2019/050900
§ 371 (c)(1),
(2) Date: Jun. 30, 2021

(87) PCT Pub. No.: WO2020/141249
PCT Pub. Date: Jul. 9, 2020

(65) Prior Publication Data
US 2022/0009855 A1   Jan. 13, 2022

(30) Foreign Application Priority Data
Dec. 31, 2018  (FI) ...................................... 20186143

(51) Int. Cl.
*C07C 45/48*   (2006.01)
*C07C 1/213*   (2006.01)
(Continued)

(52) U.S. Cl.
CPC ............. *C07C 45/48* (2013.01); *B01J 21/063* (2013.01); *C07C 1/213* (2013.01); *C07C 1/24* (2013.01);
(Continued)

(58) Field of Classification Search
CPC . C07C 1/213; C07C 1/24; C07C 45/48; B01J 21/063; C11C 3/003; C11C 3/04;
(Continued)

(56) References Cited

U.S. PATENT DOCUMENTS 3,078,637 A    2/1963  Milton
9,120,713 B2 *  9/2015  Kettunen ............... B01J 23/883
(Continued)

FOREIGN PATENT DOCUMENTS

CN    107673952 A    2/2018
CN    108325535 A    7/2018
(Continued)

OTHER PUBLICATIONS

Pacchioni, G., Ketonization of carboxylic acids in biomass conversion over TiO2 and ZrO2 surfaces: a DFT perspective, Catalysis, American Chemical Society, vol. 4, pp. 2874-2888 (Year: 2014).*
(Continued)

*Primary Examiner* — Yate' K Cutliff
(74) *Attorney, Agent, or Firm* — Buchanan Ingersoll & Rooney PC (57) ABSTRACT

The present disclosure relates to a method for producing renewable ketones, paraffin waxes, base oil components and alkenes from a feedstock of biological origin, wherein the method includes ketonisation of esters of fatty acids and monohydric alcohols wherein the alcohols have carbon chain length of two or more.

27 Claims, 3 Drawing Sheets

(51) Int. Cl.
| | |
|---|---|
| C11C 3/00 | (2006.01) |
| C10M 101/02 | (2006.01) |
| C10M 177/00 | (2006.01) |
| C07C 1/24 | (2006.01) |
| C11C 3/12 | (2006.01) |
| B01J 21/06 | (2006.01) |
| C10G 3/00 | (2006.01) |
| C10G 45/64 | (2006.01) |
| C08L 91/06 | (2006.01) |
| C11C 3/04 | (2006.01) |
| C11C 3/10 | (2006.01) |
| C10N 30/02 | (2006.01) |
| C10N 70/00 | (2006.01) |

(52) U.S. Cl.
CPC .......... *C08L 91/06* (2013.01); *C10G 3/50* (2013.01); *C10G 45/64* (2013.01); *C10M 101/025* (2013.01); *C10M 177/00* (2013.01); *C11C 3/003* (2013.01); *C11C 3/04* (2013.01); *C11C 3/10* (2013.01); *C11C 3/12* (2013.01); *C10G 2300/1011* (2013.01); *C10G 2300/4006* (2013.01); *C10G 2300/4012* (2013.01); *C10G 2300/4018* (2013.01); *C10G 2400/10* (2013.01); *C10M 2203/1025* (2013.01); *C10N 2030/02* (2013.01); *C10N 2070/00* (2013.01)

(58) Field of Classification Search
CPC .. C11C 3/10; C11C 3/12; C08L 91/06; C10M 101/025; C10G 3/50
See application file for complete search history.

(56) References Cited

U.S. PATENT DOCUMENTS

| | | | |
|---|---|---|---|
| 9,314,785 B1* | 4/2016 | Hommeltoft | ............ C07C 45/48 |
| 2012/0083633 A1 | 4/2012 | Aulich et al. | |
| 2013/0150638 A1* | 6/2013 | Koivusalmi | .............. C07C 1/22 |
| | | | 585/251 |
| 2014/0221675 A1 | 8/2014 | Agarwal | |

FOREIGN PATENT DOCUMENTS

| | | |
|---|---|---|
| EP | 1741768 A1 | 1/2007 |
| EP | 2155838 B1 | 9/2014 |
| EP | 3012310 A1 | 4/2016 |
| FI | 100248 B | 10/1997 |
| WO | 2007068795 A1 | 6/2007 |
| WO | 2008152200 A1 | 12/2008 |
| WO | 2013113976 A1 | 8/2013 |
| WO | 2015181721 A1 | 12/2015 |
| WO | 2016062868 A1 | 4/2016 |
| WO | 2016123198 A1 | 8/2016 |
| WO | 2018020321 A1 | 2/2018 |
| WO | 2018178130 A1 | 10/2018 |
| WO | 2018193074 A1 | 10/2018 |
| WO | 2018234187 A1 | 12/2018 |
| WO | 2018234188 A1 | 12/2018 |
| WO | 2018234189 A1 | 12/2018 |

OTHER PUBLICATIONS

Alm, Martin, "Animal Fats," The European Fat Processors and Renderers Association, Brussels, Belgium, 2013, AOCS Lipid Library, The American Oil Chemists' Society. (19 pages).

ASTM International Designation:D6866-16, "Standard Test Methods for Determining the Biobased Content of Solid, Liquid, and Gaseous Samples Using Radiocarbon Analysis", ASTM International, Conshohocken, PA, US. (19 pages).

Cermak, Steven C., et al., "Distillation of Natural Fatty Acids and Their Chemical Derivatives", Distillation-Advances from Modeling to Applications, pp. 5, 110-140, Dr. Sina Zereshki (Ed.), ISN: 978-953-51-0428-5, InTech. (34 pages).

Finnish Search issued in corresponding Finnish Patent Application No. 20186145 dated Apr. 29, 2019. (2 pages).

Finnish Search Report issued in corresponding Finnish Patent Application No. 20186143 dated Apr. 24, 2019. (1 page).

Finnish Search Report issued in corresponding Finnish Patent Application No. 20186144 dated Apr. 29, 2019. (2 pages).

Handbook on Automobile & Allied Products 2nd Revised Edition, 2013, Ajay Kr Gupta, 10 Lube Oil, Base Oil, Mineral Oil, p. 117. (1 page).

International Search Report (PCT/ISA/210) and Written Opinion (PCT/ISA/237) dated Apr. 1, 2020, by the Finnish Patent and Registration Office as the International Searching Authority for International Application No. PCT/FI2019/050917. (15 pages).

International Search Report (PCT/ISA/210) and Written Opinion (PCT/ISA/237) dated May 15, 2020, by the Finnish Patent and Registration Office as the International Searching Authority for International Application No. PCT/FI2019/050900. (13 pages).

Lin, X., et al., "Hydrogenolysis of Glycerol by the Combined Use of Zeolite and Ni/Al2O3 as Catalysts: A route for Achieving High Selectivity to 1-Propanol," energy&fuels, Apr. 17, 2014, pp. 3345-3351, vol. 28, ACS Publications. (7 pages).

Moss, G.P., et al., "Glossary of Class Names of Organic Compounds and Reactive Intermediates Based on Structure", Pure & Appl. Chem., 1995, pp. 1307-1375, vol. 67, Nos. 8/9, IUPAC, Great Britain. (69 pages).

Van Ryneweld, E., et al., "A catalytic route to lower alcohols from glycerol using Ni-supported catalysts," Green Chemistry, 2011, pp. 1819-1827, vol. 13, The Royal Society of Chemistry. (10 pages).

Zhu, S., et al., "One-step hydrogenolysis of glycerol to biopropanols over Pt-$H_4SiW_{12}O_{40}/ZrO_2$ catalysts", Green Chemistry. 2012, pp. 2607-2616, vol. 14, The Royal Society of Chemistry. (11 pages).

Office Action dated Aug. 31, 2021, by the Canadian Patent Office in corresponding Canadian Patent Application No. 3,122,907. (4 pages).

* cited by examiner

PROCESS FOR PRODUCING RENEWABLE PRODUCTS

FIELD

The present invention relates to processes for producing renewable products, such as ketones, oil products and olefins, in particular to methods including ketonisation reaction of fatty acid esters.

BACKGROUND

Renewable feedstocks present a sustainable alternative to petrochemical sources. The renewable feedstock has been derived from e.g. variety of vegetable oils, animal fats, recycled waste oils and even microbial oils. Hydrotreated vegetable oils such as palm oil, derivatives thereof, animal fat and other wastes or residues have been the major feedstock dominating the global renewable fuel market.

In addition to fuels, fats and oils can be step-by-step processed into renewable chemicals and base oils. One of these processes includes ketonisation, which enables removal of the highly reactive carboxylic functional groups while increasing the carbon chain length. The formed ketones are building blocks for further condensation, e.g. hydrodeoxygenation, to obtain suitable products for the required applications.

WO2008/152200 A1 discloses a method for producing base oils comprising subjecting a feedstock comprising various oxygen containing organic molecules, including free fatty acids and fatty acid esters, to a condensation reaction and subsequent hydrodefunctionalization and isomerization reaction.

WO2007/068795 A1 discloses a process for producing a new type of high-quality hydrocarbon base oil of biological origin. The process comprises ketonisation, hydrodeoxygenation, and isomerization steps. Fatty acids and/or fatty acid esters based on a biological raw material are preferably used as the feedstock.

The ketonisation reaction is commonly performed by using carboxylic acids as starting materials due to their high reactivity. However, free fatty acids are highly corrosive and special type of reactors for the ketonisation reaction are required.

Corrosion free ketonisation would be desirable, since it allows the use of significantly more economical materials for processing.

Ethene is a platform petrochemical produced by several methods. A primary method is steam cracking where hydrocarbons and steam are heated to 750-950° C. This process converts large hydrocarbons into smaller ones and introduces unsaturation. Ethene is separated from the resulting mixture by repeated compression and distillation. Other technologies employed for the production of ethene include oxidative coupling of methane, Fischer-Tropsch synthesis, methanol-to-olefins and catalytic dehydrogenation.

Renewable ethene may be produced from renewable ethanol (from biomass) which can be obtained by fermentation of sucrose feedstock and from starchy biomass by hydrolysis followed by fermentation or from ligno-cellulosic biomass.

However, there is still a need for further efficient methods that can process low-value biological feedstocks into high-value products.

SUMMARY

The following presents a simplified summary in order to provide a basic understanding of some aspects of various invention embodiments. The summary is not an extensive overview of the invention. It is neither intended to identify key or critical elements of the invention nor to be restricted thereto. The following summary merely presents some concepts of the invention in a simplified form as a prelude to a more detailed description of exemplifying embodiments of the invention.

It was observed in the present invention that when a feedstock comprising esters of fatty acid and monohydric alcohols, wherein the alcohol has a carbon chain length of two or more, i.e. ethyl, propyl, butyl, etc. esters of the fatty acids, was ketonized in the presence of metal oxide ketonisation catalyst, not only the corresponding ketone but also an olefin was obtained. Advantageously, the ketonisation reaction does not require corrosion-resistant reactors, and in addition renewable alkene is simultaneously produced.

Accordingly, it is an object of the present invention to provide a method for simultaneously producing renewable ketones and alkenes from a feedstock of biological origin, the method comprising the following steps:
a) providing a feedstock comprising fatty acids and/or fatty acid esters,
b) subjecting the feedstock to esterification reaction in the presence of a monohydric alcohol, wherein the monohydric alcohol has a carbon chain length of two or more, yielding esters of the fatty acids and the monohydric alcohol, in proviso that when the feedstock comprises esters of fatty acids and monohydric alcohol wherein the monohydric alcohol has a carbon chain length of two or more, step b) is optional,
c) subjecting the esters of the fatty acids and the monohydric alcohol to ketonisation reaction in the presence of a metal oxide ketonisation catalyst, yielding an intermediate product stream comprising ketones, alkenes, and carbon dioxide, and
d) separating the alkenes from the intermediate product stream yielding an alkene depleted intermediate product stream and the separated alkenes.

It is another object of the present invention to provide a method for producing renewable wax from a feedstock of biological origin, the method comprising subjecting the alkene depleted intermediate product stream obtained to hydrodeoxygenation reaction.

It is still another object of the present invention to provide a method for producing renewable base oil fulfilling the API Group III base oil specifications having ≥90 wt % saturated hydrocarbons, ≤0.03 wt-% sulphur and a viscosity index of ≥120 from a feedstock of biological origin, the method comprising subjecting the alkene depleted intermediate product stream obtained to both hydrodeoxygenation reaction and to hydroisomerisation reaction, simultaneously or in sequence, to yield a deoxygenated and isomerized product stream comprising renewable base oil components.

A number of exemplifying and non-limiting embodiments of the invention are described in accompanied dependent claims.

Various exemplifying and non-limiting embodiments of the invention together with additional objects and advantages thereof, will be best understood from the following description of specific exemplifying and non-limiting embodiments when read in connection with the accompanying figures.

The verbs "to comprise" and "to include" are used in this document as open limitations that neither exclude nor require the existence of also un-recited features. The features recited in dependent claims are mutually freely combinable unless otherwise explicitly stated. Furthermore, it is to be understood that the use of "a" or "an", i.e. a singular form, throughout this document does not exclude a plurality.

DESCRIPTION

The specific examples provided in the description below should not be construed as limiting the scope and/or the applicability of the accompanied claims. Lists and groups of examples provided in the description are not exhaustive unless otherwise explicitly stated.

As defined herein base oil is an oil product which is suitable for use as a lubricant component.

The American Petroleum Institute (API) divides base oils into five main groups shown in table 1. Groups I-III are petroleum base oil of varying qualities.

TABLE 1

| API base stock categories | | | |
|---|---|---|---|
| Group | Sulfur, wt-% | Saturates, % | Viscosity Index (VI) |
| I | >0.03 | and/or <90 | 80 – 119 |
| II | ≤0.03 | and ≥90 | 80 – 119 |
| III | ≤0.03 | and ≥90 | ≥120 |
| IV | Synthetic poly-alpha-olefins (PAOs) | | |
| V | Any other type of base oil than group I-IV | | |

The API defines the differences between Group II and III only in terms of the viscosity index (VI), and the Group III base oils are also called very high viscosity base oils (VHVI). However, also cold flow properties, viscosity level as well as Noack volatility number are important characteristics of base oils. The renewable base oil of the present invention fulfills the API Group III base oil specifications, having ≥90 wt-% saturated hydrocarbons, ≤0.03 wt-% sulfur and a viscosity index of ≥120.

Lubricant industry commonly extends the Group terminology of table 1 to include [Handbook on Automobile & Allied Products 2$^{nd}$ Revised Edition, 2013, Ajay Kr Gupta, 10 Lube Oil: page 117]:
Group I+: as Group I but with viscosity index of 103-108
Group II+: as Group II but with viscosity index of 113-119
Group III+: as Group III but with viscosity index of at least 140.

According to a preferable embodiment renewable base oil of the present invention fulfils the API Group III+ base oil specifications, having ≥90% by weight saturated hydrocarbons, ≤0.03% by weight sulphur and a viscosity index of ≥140.

As defined herein ketonisation reaction is a reaction producing a ketone through a chemical reaction of two compounds, in particular by reaction between the acyl groups in two fatty acids or in two fatty acid esters.

As defined herein the feedstock is of biological origin. As further defined herein the renewable content of the feedstock is of biological origin is determined from the starting materials, as well as being determined in the products by isotopic distribution involving $^{14}C$, $^{13}C$ and/or $^{12}C$ as described in ASTM D6866.

As defined herein deoxygenation is a method for removal of covalently bound oxygen from organic molecules.

As defined herein hydrogenation is a method for saturation of carbon-carbon double bonds by means of molecular hydrogen under the influence of a catalyst.

As defined herein fatty acids refer to carboxylic acids of biological origin, having carbon chain length of more than C1.

As defined herein fatty acid esters refer to triglycerides, fatty acid alkyl esters, esters of fatty acids with fatty alcohols, and natural waxes, all being of biological origin.

According to one embodiment the present invention relates to a method for simultaneously producing renewable ketones and alkenes from a feedstock of biological origin. The method comprises the following steps:

a) providing a feedstock comprising fatty acids and/or fatty acid esters, b) subjecting the feedstock to esterification reaction in the presence of a monohydric alcohol, wherein the monohydric alcohol has a carbon chain length of two or more, yielding an ester of the fatty acid and the monohydric alcohol, c) subjecting the ester of the fatty acid and the monohydric alcohol to ketonisation reaction conditions in the presence of a metal oxide ketonisation catalyst, yielding an intermediate product stream comprising ketones, alkenes, water and carbon dioxide, and d) separating the alkenes from the intermediate product stream yielding alkene depleted intermediate product stream and separated alkenes.

According to one embodiment, the feedstock comprises fatty acids. According to this embodiment, the fatty acids are esterified with a monohydric alcohol which has a carbon chain length of two or more, such as ethanol. The reaction is preferably catalyzed with acid. The reaction produces ester of the fatty acid and the alcohol, and water as shown in scheme 1.

Scheme 1

According to another embodiment, the feedstock comprises fatty acid methyl esters. According to this embodiment, the fatty acid methyl esters are treated with a monohydric alcohol which has a carbon chain length of two or more, such as ethanol in the presence of base. Here the esterification reaction is transesterification reaction and it produces ester of the fatty acid and the monohydric alcohol having carbon number two or more, i.e. ethanol, and methanol as shown is scheme 2.

Scheme 2

According to another embodiment, the feedstock comprises glycerides. According to this embodiment, the glycerides are treated with monohydric alcohol which has a carbon chain length of two or more, such as ethanol, in the presence of base. The transesterification reaction produces esters of the fatty acids and the monohydric alcohol having carbon number two or more and glycerol as shown in scheme 3.

Scheme 3

According still another embodiment the feedstock comprises esters or fatty acids and monohydric alcohols which has a carbon chain length of two or more, such as fatty acid ethyl esters, free fatty acids, and triglycerides. According to this embodiment the free fatty acids are first esterified with e.g. ethanol using acid as a catalyst to produce fatty acid ethyl ester and water, followed by base catalyzed transesterification of the triglycerides producing fatty acid ethyl esters and glycerol as shown in scheme 4.

Scheme 4

Only when the feedstock comprises significant amounts of fatty acid esters, wherein the fatty acids esters are esters of fatty acids and monohydric alcohols having a carbon chain length of two or more, step b) can be omitted. According to this embodiment the method comprises providing a feedstock comprising ester of fatty acid and a monohydric alcohol, wherein the monohydric alcohol has a carbon chain length of two or more, subjecting the ester of the fatty acid and the monohydric alcohol to ketonisation reaction conditions in the presence of a metal oxide ketonisation catalyst, yielding an intermediate product stream comprising ketones, alkenes, water and carbon dioxide, separating the alkenes from the intermediate product stream yielding alkene depleted intermediate product stream and separated alkenes.

According to an exemplary embodiment the feedstock comprises at least 25% by weight, preferably 50% by weight, more preferably, at least 75% by weight, most preferably at least 90% by weight esters of fatty acid and a monohydric alcohol, wherein the alcohol has a carbon number of two or more. According to these embodiments, the feedstock may be subjected to ketonisation without esterification.

In one embodiment, a purification step is included into the method before the esterification step b) or before the ketonisation step c). A preferred purification method is fractional distillation.

The esterification of step b) may include esterification of free fatty acids of the feedstock, preferably using an acid catalyst, or transesterification of the triglyceridic renewable oil of the feedstock, preferably by conventional alkaline catalysis or solid catalyst.

According to a particular embodiment the feedstock comprises fatty acid methyl esters (FAMEs), and the esterification of step b) comprises treating the FAMEs with an excess of a monohydric alcohol having carbon chain length of two or more, such as ethanol in the presence of catalyst. The methanol formed in the transesterification reaction is separated from the desired fatty acid ethyl ester prior or during further processing.

Figure 1:
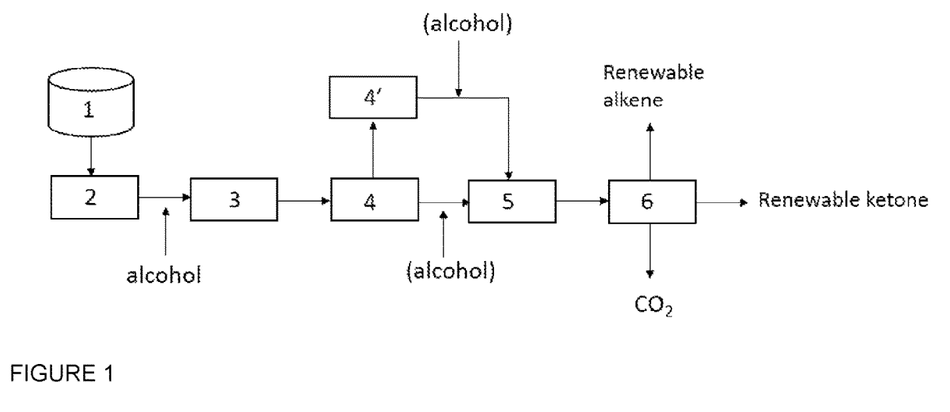
FIG. 1 shows an exemplary non-limiting schematic overview of simultaneous production of renewable ketone and alkene according to the present invention.

FIG. 1 describes an exemplary non-limiting method for simultaneously producing renewable ketones and renewable alkenes from a feedstock of biological origin. In the figure reference numbers and arrows illustrate reactions and streams, respectively.

Accordingly, the feedstock 1 comprising fatty acids and/or fatty acid esters is optionally subjected to purification step 2, e.g. by distillation, to give a purified feedstock. The feedstock or the purified feedstock is subsequently subjected to an esterification step 3 with a monohydric alcohol, wherein the alcohol has a carbon chain length of two or more. The esters obtained may optionally be subjected to fractionation 4, preferably by distillation, or to further purification step 4', before entering into a ketonisation step 5. The intermediate product stream is directed from the ketonisation to a separation step 6 wherein the formed alkenes and $CO_2$ are separated from the ketones, forming the alkene depleted intermediate stream comprising the ketones.

In case the feedstock comprises significant amounts, e.g. 25% by weight or more of esters of fatty acids and a monohydric alcohol, wherein the alcohol has a carbon chain length of two or more, the esterification step of FIG. 1 can be omitted, or at least that fraction of the feedstock comprising the esters of fatty acids and the monohydric alcohol wherein the alcohol has a carbon chain length of two or more can be processed further without the esterification step. According to a preferable embodiment, the process includes separating the desired fraction, preferably by distillation, from the feedstock.

According to a particular embodiment, a monohydric alcohol is added to the ketonisation step 5. Dehydroxylation of the alcohol produces water which in turn alleviates coke formation of the ketonisation catalyst. Furthermore, the alcohol fed may produce alkenes during the ketonisation reaction conditions thus increasing the total yield of the alkenes formed.

The monohydric alcohols are preferably renewable alcohols, such as renewable ethanol, renewable propanol or renewable butanol, preferably renewable ethanol, produced according the state of art.

The ketonisation reaction thus produces renewable ketones, renewable alkenes and renewable carbon dioxide.

Figure 2:
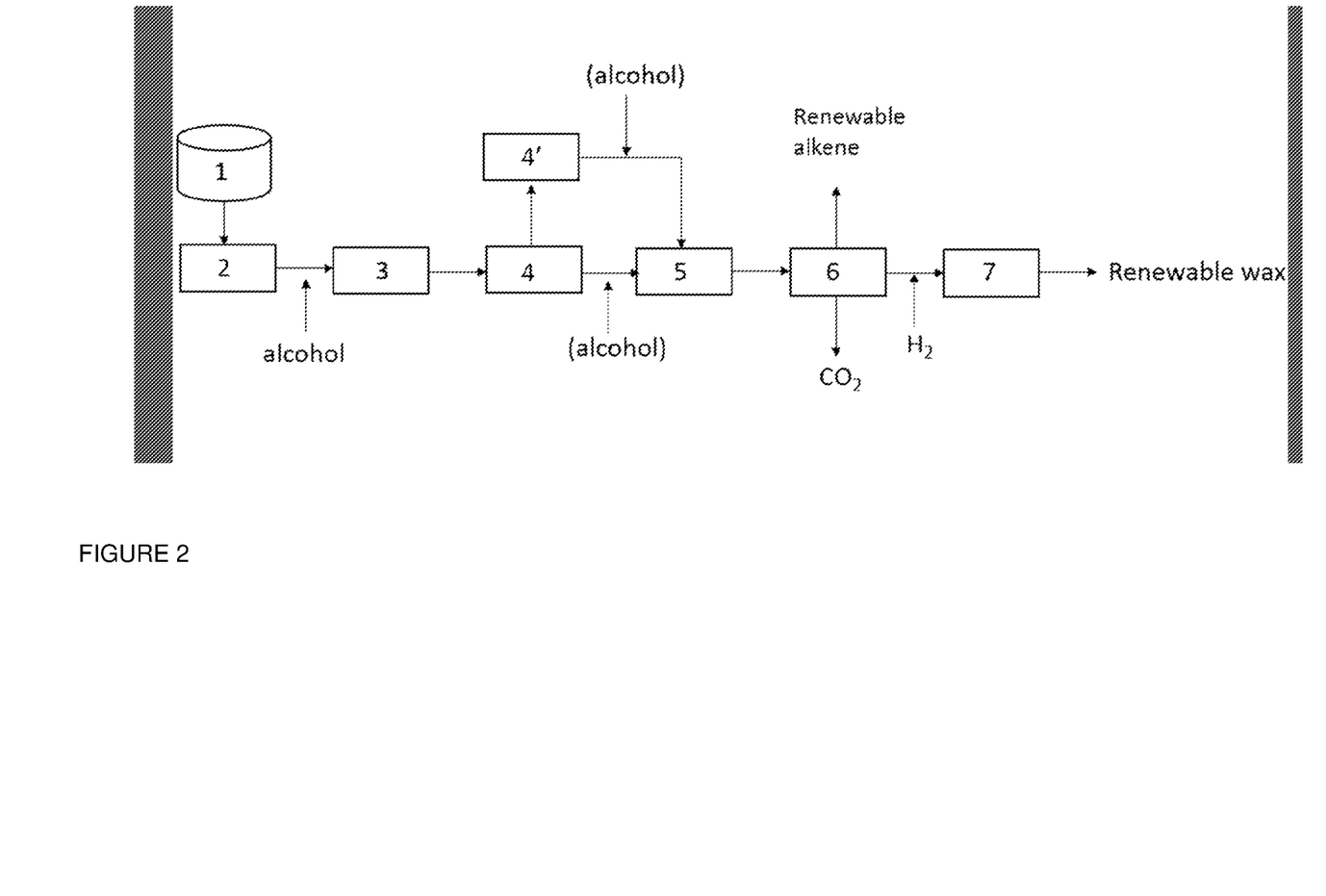
FIG. 2 shows an exemplary non-limiting schematic overview of production of renewable wax and alkene according to the present invention.

FIG. 2 describes an exemplary non-limiting method for producing renewable wax and renewable alkenes from a feedstock of biological origin. The method is as disclosed in FIG. 1 for producing renewable ketones and renewable alkenes, but the alkene depleted intermediate product stream obtained is subjected to a further hydrodeoxygenation step 7.

Figure 3:
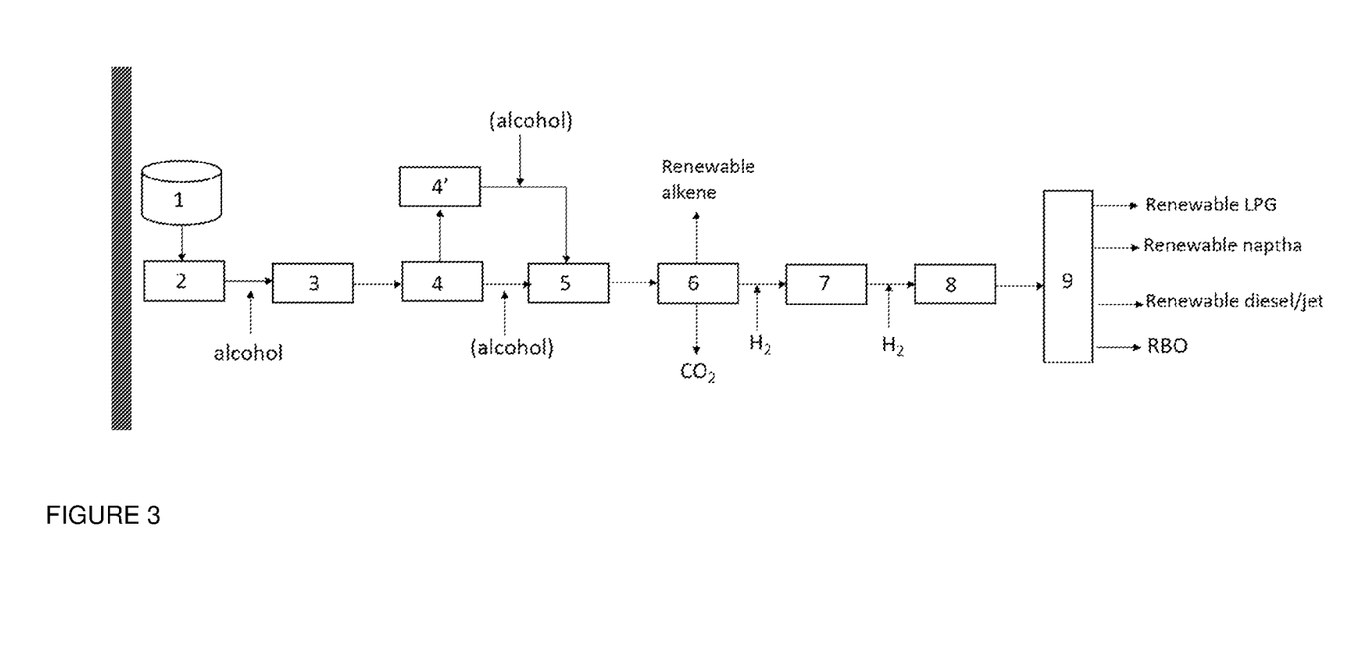
FIG. 3 an exemplary non-limiting schematic overview of production of renewable base oil components and alkene according to the present invention.

FIG. 3 describes an exemplary non-limiting method for producing alkenes together with several renewable hydrocarbon components, such as renewable liquid petroleum gas (LPG), renewable naphtha, renewable diesel, renewable jet fuel, and renewable base oil (RBO) from a feedstock of biological origin. The method is as disclosed in FIG. 2 for producing renewable wax and renewable alkenes, but the hydrodeoxygenation step 7 is followed by an isomerization step 8. Although shown in the figure as two different reactions, the hydrodeoxygenation reaction and the hydroisomerisation reaction can be performed simultaneously in a single step or in sequence, to yield a deoxygenated and isomerized product stream comprising the renewable hydrocarbon components. The obtained product stream can be subjected to a further separation step 9 to separate the renewable hydrocarbon components e.g. by distillation.

The processes of the present invention are described in more detail below.

The feedstock for use in the present invention may comprise fatty acids and/or fatty acid esters originating from renewable sources, such as vegetable oils, plant oils, fish oils, animal fats, algae and oils obtained from native or GMO microbes, such as yeast and mold.

As defined herein animal fats are a by-product of the whole meat chain. Animal fats are not produced as such. They are only produced in relation to the raising of animals for meat, eggs, milk or wool production. Animal fats are a side, co- or by-product of the production of another animal product (Alm, M., (2013) Animal fats. Available at http://lipidlibrary.aocs.org/OilsFats/content.cfm?ItemNumber=40320, accessed 21 Dec. 2018).

The fatty acid esters may comprise triglycerides. The feedstock may comprise 0-100% glycerides and 0-100% free fatty acids. If the method comprises a transesterification reaction, the feedstock comprises preferably less than 0.5% by weight free fatty acids.

Particular feedstock suitable for the method of the present invention is low-value palm fatty acid distillate (PFAD) which typically contains 10-20% glycerides or waste animal fat which typically contains 80-90% glycerides, which are not suitable for food/feed applications. A particular feedstock comprises C16 fatty acid containing glycerides.

According to the present invention, free fatty acids and fatty acid glycerides of the feedstock are converted to esters of fatty acid and monohydric alcohols, wherein the monohydric alcohol has a carbon chain length of two or more. Naturally, if the feedstock comprises predominantly esters of fatty acids and monohydric alcohols having a carbon chain length of two or more, the esterification step can be omitted.

According to one embodiment fatty acid esters like triglycerides are transesterified with an alcohol to obtain fatty acid alkyl esters. A monohydric alcohol having a carbon chain length of two or more is used as the alcohol, and sodium and potassium hydroxides dissolved in excess of the alcohol may be used as catalysts. Typical conditions for transesterification may comprise temperature from 60 to 70° C. and pressure from atmospheric pressure to 2 MPa.

Due to saponification of free fatty acids (FFA) with very alkaline sodium methoxide catalyst ($R-CO_2H + NaOCH_3 \rightarrow R-CO_2Na + CH_3OH$), FFAs have to be removed or esterified prior to conventional transesterification reaction. Acid catalyzed transesterification is very slow and therefore esterification of fatty acids can be done prior to transesterification. Optionally FFAs can be removed by distillation (deodorization step) prior to the transesterification step.

Esterification of free carboxylic acids with alcohol requires typically higher temperature and pressure (e.g. 240° C. and 9 MPa) when using an acidic catalyst. Alternatively, free fatty acids may be separately esterified for instance using a sulfuric acid catalyst.

The monohydric alcohol applied in the method of the present invention is preferably renewable alcohol. Exemplary carbon chain length of the alcohol is from 2 to 24, preferably from 2 to 10, more preferably from 2 to 4 i.e. ethanol, propanol or butanol. Preferred alcohols are ethanol, propanol and butanol.

A particularly suitable alcohol is ethanol. A particular fatty acid ester used in the method of the present invention is ethyl ester of palmitic acid shown below.

When the alcohol is ethanol and propanol, the method produces renewable ethene and renewable propene, respectively. These components are useful starting materials for production of polyolefins. Although propanol may not be, in general bio-based, it can be produced e.g. from glycerol. The butene produced from ester of fatty acid ester and butanol used in the method of the present invention is suitable for e.g. as a starting material for alkylating agents for fuel components.

The olefins produced according to the method of the present invention are suitable e.g. as co-reagents of metathesis of fatty acids and for use in hydroformylations when producing special alcohols via aldehydes.

According to one embodiment, the ester of fatty acid and the alcohol having a carbon chain length of two or more is purified prior to ketonisation. An exemplary purification method is distillation, but also guard bed and conventional renewable oil purification methods such as degumming and/or bleaching may be used. Distillation may be used simultaneously in the selection of fatty acid/ester carbon number. This will control the viscosity of the base oil end product.

The method of the present invention includes subjecting the ester of the fatty acid to ketonisation reaction conditions in the presence of a metal oxide ketonisation catalyst. According to a particular embodiment a monohydric alcohol having carbon chain length of two or more is added directly to the ketonisation step. The monohydric alcohol is preferably purified alcohol, more preferably the alcohol amount is more than 95 w-%, rest being e.g. water, but not containing any metals or other elements.

The ketonisation reaction has typically been carried out under ketonisation conditions in the presence of various metal oxide catalysts, such as CaO, MnO, or MgO or double metal oxides like $K_2O/TiO_2$. According to a preferable embodiment the metal oxide comprises $TiO_2$ as active catalyst material. An exemplary catalyst is $TiO_2$ or $K_2O/TiO_2$-catalyst. The $TiO_2$ ketonisation catalyst may be in anatase form having an average pore diameter of 80-160 Å, and/or a BET area of 20-140 $m^2/g$, and/or porosity of 0.1-0.3 $cm^3/g$ and crystallinity 50-100%. Optionally, the ketonisation catalyst is on a support. The preferred support materials include aluminum oxide, silicon oxide, titanium oxide. An advantage in using $TiO_2$ is that this catalyst is simultaneously active in ketonisation reaction and alkene forming reaction, and withstands water and $CO_2$ formed. Furthermore, $TiO_2$ is mechanically and chemically more robust compared to several other metal oxide catalysts, and it is less likely to produce high molecular weight by-products.

According to a preferable embodiment, the ketonisation feed is introduced in liquid form into the pressurised reactor, and the ketonisation reaction is carried out at least partly, in liquid phase.

The ketonisation reaction conditions may comprise one or more of the following: a temperature in the range from 100 to 500° C. preferably from 300 to 400° C. more preferably from 350 to 360° C.; a pressure in the range from atmospheric pressure to 10 MPa, preferably from 0.5 to 5 MPa, more preferably from 1 to 3 MPa, most preferably from 1.5 to 2.5 MPa. WHSV is preferably in the range from 0.25-3 $h^{-1}$.

According to an exemplary embodiment the ketonisation reaction of step c) is performed at a temperature from 300 to 400° C. and at a pressure from 1 to 3 MPa, preferably from 1.5 to 2.5 MPa.

According to another embodiment the ketonisation reaction of step c) is performed at a temperature in the range from 100 to 500° C., preferably from 300 to 400° C., and at a pressure in the range from atmospheric pressure to 10 MPa, more preferably from 0.5 to 3 MPa, in the presence of a ketonisation catalyst.

The ketonisation reaction may be performed in the presence of an added gas, preferably in the range from 0.1 to 1.5 gas/feed ratio (w/w), wherein the feed is the fatty acid ester feed. The gas may be selected from one or more of: $CO_2$, $H_2$, $N_2$, $CH_4$, $H_2O$. A preferred gas is hydrogen. A particularly preferred gas is $CO_2$. The gas used for pressurization is advantageously $CO_2$ as it is produced as a co-product of the ketonisation reaction and can be recycled as a pressurization gas, or it may be sold for further chemical applications, such as for production of carbonates, acrylates, polymers, syngas, methane, methanol, urea and formic acid. Furthermore, $CO_2$ can be used as a feedstock to produce fuels, for example, in the Fischer-Tropsch process.

According to an exemplary embodiment the ketonisation reaction of step c) is performed in the presence of gas flow, preferably in the presence of $CO_2$ flow of 0.5-1.0 kg $CO_2$/kg ester feed.

According to a preferable embodiment the ketonisation step c) comprises adding monohydric alcohol having a carbon chain length of two or more to the ketonisation reaction.

The ketonisation reaction conditions may be selected to ensure liquid phase ketonisation or at least that the feed introduction to the ketonisation step is in liquid form. Liquid phase ketonisation, by suitable selection of a combination of catalyst, pressure and temperature, ensures high activity and good selectivity. Gas phase ketonisation requires high gas recycle rate in order to transfer fatty acid esters from solid or liquid form into gas phase, due to the high boiling points of fatty acid esters. This means that the reactor system for the gas phase ketonisation needs to be larger and more complex which in turn increases investment costs significantly.

It was also surprisingly found that the ketonisation of an ester of fatty acid and a monohydric alcohol having a carbon chain length of two i.e. ethyl ester produced the desired ketone in higher selectivity and yield than e.g. the corresponding methyl ester.

According to the method of the present invention the intermediate product stream comprises ketones and alkenes. For example, if the fatty acid ester feed is exclusively palmitic acid ethyl ester, such as C16 fatty acid ester, the intermediate product stream will comprise C31 ketone and ethene, and if the fatty acid ester feed is a mixture of ethyl ester of C16 and C18 fatty acids, the intermediate product stream will comprise a mixture of C31, C33, and C35 ketones and ethene. Analogously, if the fatty acid ester feed is exclusively palmitic acid butyl ester, the intermediate product stream will comprise C31 ketone and butene.

The ketonisation reaction produces also carbon dioxide. Since the ketonisation reaction is clean and substantially quantitative, the method is also suitable for producing very pure renewable $CO_2$ for various applications. Exemplary applications may be use e.g. for soft drinks, propellant gas, and for cooling or for production of chemicals.

The fatty acids and fatty acid esters present in the feedstock may have a high degree of unsaturation.

If the fatty acid esters contain unsaturated fatty acid esters, these fatty acids esters are preferably saturated by hydrogenation prior to ketonisation. Such a prehydrogenation step is usually conducted under rather mild conditions in the presence of a hydrogenation catalyst at temperatures from 50 to 400° C., under a hydrogen pressure ranging from atmospheric pressure to 20 MPa, preferably at temperatures from 150 to 300° C., under a hydrogen pressure ranging from 1 to 10 MPa. The prehydrogenation catalyst contains metals of the Group VIII and/or VIA of the periodic system of the elements. The prehydrogenation catalyst is preferably a supported Pd, Pt, Rh, Ru, Ni, Cu, CuCr, NiMo or CoMo catalyst, the support being activated carbon, alumina and/or silica. The prehydrogenation step may be performed also prior to esterification and/or transesterification step b), i.e.

the initial feedstock is prehydrogenated. However, it is desirable that no hydrogenation of carboxylic group is done. For example, palmitic acid (saturated free fatty acid) in PFAD may be separated by distillation, thus yielding a saturated free fatty acid feed of palmitic acid without any hydrogenation necessary. Esterification of the free fatty acid feed then produces saturated fatty acid ester feed.

According to the method of the present invention the alkene produced is separated from the intermediate product stream producing an alkene depleted intermediate product steam and a separated alkene. Applicable separation methods include stripping, flash drum operation and distillation. In the case of stripping or flash drum operation, sudden pressure drop makes the gas/liquid separation easier even at high temperature. Removal of $CO_2$ may be performed e.g. by adsorption to zeolitic molecular sieve as disclosed in U.S. Pat. No. 3,078,637.

According on an embodiment the method of the present invention comprises producing renewable wax. According to this embodiment the alkene depleted intermediate product stream is subjected to hydrodeoxygenation reaction. The obtained product is a deoxygenated base oil stream comprising the renewable n-paraffin wax. N-paraffins can be isomerised in order to obtain base oil components with satisfactory cold flow properties.

The hydrodeoxygenation reaction may be performed in the presence of a hydrodeoxygenation catalyst, such as CoMo, NiMo, NiW, CoNiMo on a support, for example an alumina support. The hydrodeoxygenation catalyst may be typical hydrodeoxygenation catalysts in the art e.g. those described in PCT/EP2018/065973, for example it may comprise a hydrogenation metal on a support, such as a catalyst selected from a group consisting of Pd, Pt, Ni, Co, Mo, Ru, Rh, W or any combination of these. The hydrodeoxygenation step is done under hydrodeoxygenation conditions to provide the renewable base oil product. The hydrodeoxygenation step may for example be conducted at a temperature of 100 to 500° C. preferably 250-400° C. and at a pressure of range from atmospheric pressure to 20 MPa, preferably from 0.1 to 8 MPa, more preferably from 0.2 to 8 MPa; a preferably a WHSV in the range from 0.5 to 3 h$^{-1}$, and preferably a $H_2$ flow of 350-900 nl $H_2$/l feed in the presence of a hydrodeoxygenation catalyst. The catalyst may be NiMo on alumina or silica support.

According to an exemplary embodiment the hydrodeoxygenation reaction is performed at temperature in the range from 250 to 400° C., a pressure in the range from 2 to 8 MPa, a WHSV in the range from 0.5-3 h$^{-1}$, and a $H_2$ flow of 350-900 ml $H_2$/l feed, in the presence of a hydrodeoxygenation catalyst.

Preferably, the hydrodeoxygenation condition for ketones involves a temperature in the range from 250 to 350° C.; a pressure in the range from 3 to 6 MPa; a WHSV in the range from 1.0-2.5 h$^{-1}$; and a $H_2$/oil fed ratio of 350-750 nl/l. The catalyst is preferably NiMo on alumina support.

When the ketonisation conversion is high, preferably about complete, the hydrodeoxygenation condition may involve a temperature in the range from 300 to 330° C.; a pressure in the range from 4 to 5 MPa; a WHSV in the range from 1.0-2.0 h$^{-1}$; and a $H_2$/oil fed ratio of 350-500 nl/l. The catalyst is preferably NiMo on alumina support.

According to another embodiment the hydrodeoxygenation is done in the presence of hydrogen gas in a hydrodeoxygenation zone, which may comprise one or more catalyst beds in a fixed bed reactor, ebullated bed or CSTR continued stirred tank reactor.

According to another embodiment the present invention comprises a method for producing renewable base oil fulfilling the API Group III base oil specifications having ≥90 wt % saturated hydrocarbons, ≤0.03 wt-% sulphur and a viscosity index of ≥120, preferably fulfilling the API Group III+ base oil specifications having ≥90 wt % saturated hydrocarbons, ≤0.03 wt-% sulphur and a viscosity index of ≥140.

According to this embodiment the deoxygenated intermediate product stream is further subjected to hydroisomerisation reaction for branching the n-paraffins originating from the hydrodeoxygenation step. Hydroisomerisation step converts n-paraffins from hydrodeoxygenation step to isoparaffins with required cold flow properties for base oil application.

Accordingly, the product of the hydrodeoxygenation step is subjected to an isomerization step in the presence of hydrogen and an isomerization catalyst. Both the hydrotreatment step and isomerization step may be conducted in the same reactor, and even in the same reactor bed. The isomerization catalyst may be a noble metal bifunctional catalyst such as a Pt containing commercial catalyst, for example Pt-SAPO or Pt-ZSM-catalyst or for example a non-noble catalyst, such as NiW.

When a tungsten-based catalyst is used, such as a NiW, or a Pd or Pt catalyst, it has the further advantage that it can also catalyze isomerization reactions, thus enabling a simultaneous hydrodeoxygenation and hydroisomerisation reaction. Accordingly, the hydrodeoxygenation and isomerization catalyst may be the same, such as for example NiW, or a Pt catalyst, such as Pt/SAPO in mixture with a promoted Mo catalyst on a support, e.g. NiMo on alumina. The NiW catalyst may additionally result in more hydrocracking to diesel/JET fuel and naphtha products and may be an advantageous catalyst if such components are also desired to be produced together with the renewable base oil components.

The hydroisomerisation reaction is typically performed at a temperature in range from 200 to 450° C., preferably from 250 to 400° C.; a pressure in range from 1-15 MPa, preferably 1-6 MPa; preferably a WHSV in range from 0.5-3 h$^{-1}$, and preferably a $H_2$ flow of 100-800 nl $H_2$/l feed, in presence of an hydroisomerisation catalyst, such as a catalyst comprising a Group VIII metal and a molecular sieve, optionally on an alumina and/or silica support.

It is desirable to reduce the severity of the isomerization reaction to avoid or reduce the amount of cracking of the renewable base oil product. The isomerization step may, for example, be conducted at a temperature of 250-400° C., at a pressure of between 1 and 6 MPa, a WHSV of 0.5-3 h$^{-1}$, and a $H_2$/oil feed ratio of 100-800 nl/l.

Alternatively, the hydrodeoxygenation and hydroisomerisation reactions may be done in sequence. The sequence is preferably hydrodeoxygenation followed by hydroisomerisation. The isomerization reaction conditions may comprise one or more of the following: a temperature in the range from 250 to 400° C.; a pressure in the range from 1 to 6 MPa; a WHSV in the range from 0.5-3 h$^{-1}$; and a $H_2$/oil feed ratio of 100-800 nl/l.

Isomerization prior to hydrodeoxygenation provides skeletal isomerization of fatty acids, which needs double bonds and therefore favors the use of unsaturated fatty acids or unsaturated ketones. Typically, hydroisomerisation catalyst cannot withstand much S-, N-, or O-impurities.

Preferably the isomerization reaction conditions comprise a temperature in the range from 280 to 370° C.; a pressure in the range from 2 to 5 MPa; a WHSV in the range from 0.5-2.0 h$^{-1}$; a $H_2$ flow of 200-650 ml $H_2$/l feed.

More preferably the isomerization reaction conditions comprise a temperature in the range from 300 to 350° C.; a pressure in the range from 2.5 to 4.5 MPa; a WHSV in the range from 0.5-1.0 h$^{-1}$; a H$_2$ flow of 300-500 ml H$_2$/l feed.

The hydroisomerisation reaction may be performed in the presence of an isomerization catalyst, such as a catalyst comprising a Group VIII metal, preferably Pt, and a molecular sieve, optionally on support. The support may, for example, be selected from silica, alumina, clays, titanium oxide, boron oxide, zirconia, which can be used alone or as a mixture, preferably silica and/or alumina. The molecular sieve may, for example, be zeolites, such as ZSM or aluminophosphate molecular sieves, such as SAPO, such as SAPO-11, MeAPO, MeAPSO, where Me is e.g. Fe, Mg, Mn, Co or Zn, molecular sieves EIAPO or EIAPSO, e.g. silica-alumina, Y zeolite, SAPO-11, SAPO-41, ZSM-22, ferrierite, ZSM-23, ZSM-48, ZBM-30, IZM-1, COK-7. Suitable molecular sieves and characteristics of molecular sieves suitable for hydroisomerisation applications are known to the skilled person and have been described in the literature.

When the hydrodeoxygenation and hydroisomerisation takes place in sequence, in-between the hydrodeoxygenation and hydroisomerisation there may be a stripping step, wherein gasses are separated from liquids. This may take place in a high temperature and high-pressure separation step, for example at a temperature between 300-330° C. and pressure between 3-5 MPa.

According to an exemplary embodiment the isomerization reaction is performed a temperature in the range from 250 to 400° C., a pressure in the range from 1 to 6 MPa, a WHSV in the range from 0.5-3 h$^{-1}$, and a H$_2$ flow of 100-800 ml H$_2$/l feed, in the presence of an isomerization catalyst, such as a catalyst comprising a Group VIII metal and a molecular sieve, optionally on an alumina and/or silica support.

The base oil components can be further separated from the product stream. An exemplary separation is distillation. The product thus obtained is deoxygenated renewable base oil component or deoxygenated and isomerized base oil component. For example, the deoxygenated and isomerized product stream may be distilled to obtain the renewable base oil component in a fraction having a boiling point of more than 380° C., such as more than 450° C., for example more 460° C. or more, such as 470° C. or more, such as 480° C. or more, or for example 500° C. or more. For example, the distillation may yield one or more fractions of renewable base oils, for example above 380° C., for example a fraction between 380-450° C. and a fraction above 450° C.

The base oil components and base oil produced are further characterized as discussed in PCT/EP2018/065976.

EXAMPLES

The equipment used to carry out the semi-batch ketonisation test was provided by 300 mL stirred reactor system from Parr Instrument Company. Heating, temperature, pressure, mixing speed and other process variables were managed with computer connected to Parr 4848B reactor controller. The main equipment consisted of 300 mL Hastelloy-made reactor, heater, stirrer motor and mixer, temperature and pressure sensors, safety rupture disk, heating cables and valves.

The reactor system was connected to three gas lines which were used in turns based on the type and phase of the experiment: the CO$_2$-bottle for ketonisation and He from gas manifold for pre-run leak testing. CO$_2$ and H$_2$ lines were connected into a gas measurement system to adjust the gas flow rate. The pressure in the reactor was adjusted and held stable with pressure valve allowing the water and CO$_2$ to flow out towards cooled water trap container. From this container, gas was led into Ritter drum-type gas volume meter and out of the fume hood by air exhaust.

Gas analysis was performed for the experiment product gas. The sample was collected for 4 hours involving the CO$_2$ fed into reactor and the CO$_2$ formed in the reactions. The method involves the analysis of inert gases: hydrogen, oxygen, nitrogen, carbon monoxide, and carbon dioxide as well as hydrocarbons from the carbon number area C1 to C6 with Al$_2$O$_3$ column or hydrocarbons from area C1 to C12 with non-polar column through gas chromatography.

Ketonisation of Ethyl Palmitate According to the Invention

Conditions applied for ethyl palmitate ketonisation are shown in table 2.

TABLE 2

Reaction conditions of ethyl palmitate ketonisation

| Variable | value |
| --- | --- |
| Feed (ethyl palmitate) | 115 g |
| Catalyst (TiO$_2$, 0.15-0.35 mm) | 7.0 g |
| Temperature | 360° C. |
| Pressure | 20 bar |
| CO$_2$ flow | 1.0 L/h |
| Samples obtained during run | 4 |
| Total reaction time | ~5 hours |

Four samples were taken and analyzed by gas chromatography (GO). The results are shown in table 3.

TABLE 3

The conversion of ethyl ester of palmitic acid to ketones and alkene.

| Product | unit | Sample 1 1.1 h | Sample 2 3.1 h | Sample 3 4.0 h | Sample 4 4.3 h* |
| --- | --- | --- | --- | --- | --- |
| <C16:0 (Cracking, decarboxylation etc.) | wt-% | 5.3 | 11.3 | 13.4 | 14.0 |
| palmitic acid | wt-% | 40.8 | 12.7 | 5.1 | 2.7 |
| Feed: Ethyl palmitate | wt-% | 23.1 | 8.6 | 4.7 | 1.3 |
| Other Ketones | wt-% | 9.5 | 16.7 | 15.7 | 18.6 |
| Main product: C15-C15 ketone | wt-% | 20.4 | 48.2 | 58.3 | 59.5 |
| Heavies | wt-% | 0.8 | 2.4 | 2.9 | 3.9 |
| Total | wt-% | 100 | 100 | 100 | 100 |

*Last sample was taken from reactor after cooling (started at 4.0 h)

Main gas analyses are shown in table 4.

TABLE 4

Gas analysis results of hydrocarbons (ethyl ester test)

| Component | mol-% | wt-% |
|---|---|---|
| Methane | 0.3 | 0.1 |
| Ethene | 81.0 | 70.4 |
| Ethane | 7.3 | 6.8 |
| Propene | 0.3 | 0.4 |
| butenes | 1.9 | 3.4 |
| butane | 0.7 | 1.2 |
| Other alkenes | 1.1 | 2.2 |
| ethanol | 1.0 | 1.4 |
| Diethyl ether | 4.0 | 9.2 |
| Other hydrocarbons | 2.4 | 4.9 |
| total | 100.0 | 100.0 |

Table 4 shows that the major part of the organic gas formed (over 80 mol-%) is ethylene (ethene), even though the reaction was not optimized. Ethylene is the preferred co-product of the ketonisation of palmitic acid ethyl ester. Some ethanol and diethyl ether components are also observed which can also be converted to ethylene or used as is, as fuel components. Butenes formed can be used as feed for alkylate, they are also e.g. excellent gasoline components produced at many crude oil refineries.

Comparative Ketonisation of Methyl Palmitate

Ketonisation of methyl palmitate was performed as described above for ethyl palmitate. Results of gas chromatography analysis are shown in table 5.

TABLE 5

The conversion of methyl ester of palmitic acid to ketones and alkene (comparative example).

| Product | unit | Sample 1 1.1 h | Sample 2 3.0 h | Sample 3 4.0 h | Sample 4 4.3 h* |
|---|---|---|---|---|---|
| <C16:0 (Cracking, decarboxylation etc.) | wt-% | 12.7 | 13.9 | 15.7 | 18.8 |
| palmitic acid | wt-% | 28.1 | 11.2 | 3.1 | 1.0 |
| Feed: methyl palmitate | wt-% | 20.2 | 15.0 | 10.5 | 2.0 |
| Other Ketones | wt-% | 6.1 | 10.5 | 14.2 | 19.0 |
| Main product: C15-C15 ketone | wt-% | 30.4 | 42.7 | 47.0 | 46.4 |
| Heavies | wt-% | 2.5 | 6.7 | 9.5 | 12.8 |
| Total | wt-% | 100 | 100 | 100 | 100 |

*Last sample was taken from reactor after cooling (started at 4.0 h)

Table 5 shows that methyl palmitate forms also in significant amounts from the main ketone, but the formation of heavies is significantly higher than using ethyl palmitate as a feed.

Comparison of ketonisation of methyl palmitate and ethyl palmitate are shown in table 6.

TABLE 6

The comparison of methyl palmitate and ethyl palmitate ketonisation end products as analyzed by GC.

| Product, wt-% | Methyl palmitate | Ethyl palmitate |
|---|---|---|
| C15-C15 ketone | 46.4 | 59.5 |
| Cracking products | 18.8 | 14.0 |
| heavies | 12.8 | 3.9 |
| ethene from gas | none | 81.0 mol-%; 70.4 wt-% |

Table 6 shows that both ester feedstocks forms ketones, but the formation of heavies is significantly higher using methyl palmitate than using ethyl palmitate as feed. Therefore, selectivity to main ketone is better when ethyl palmitate is used as feed.

Based on the above results, main product for both methyl palmitate and ethyl palmitate is C15-C15-ketone, but the yield of the desired ketone was higher when ethyl palmitate was used as a starting material. Furthermore, relatively high heavy product formation in the case of methyl palmitate was detected compared to ethyl palmitate results. Methyl palmitate ketonisation and its further reactions also produce more cracking products. Ketonisation of ethyl palmitate, in turn proceeded more smoothly, and significant amount of high-value co-product, ethene (over 80 mol-% of hydrocarbons in gas) could be isolated.

The specific examples provided in the description given above should not be construed as limiting the scope and/or the applicability of the appended claims. Lists and groups of examples provided in the description given above are not exhaustive unless otherwise explicitly stated.

The invention claimed is:

1. A method for producing simultaneously renewable ketones and renewable alkenes from a feedstock of biological origin, the method comprising steps of:
   a) providing a feedstock of biological origin containing fatty acids and/or fatty acid esters;
   b) subjecting the feedstock to esterification reaction in a presence of a monohydric alcohol, wherein the monohydric alcohol has a carbon chain length of two or more, yielding esters of the fatty acids and the monohydric alcohol, in proviso that when the feedstock includes esters of fatty acids and a monohydric alcohol, wherein the monohydric alcohol has a carbon chain length of two or more, step b) is optional;
   c) subjecting the esters of the fatty acid and the monohydric alcohol to ketonisation reaction in a presence of a metal oxide ketonisation catalyst, yielding an intermediate product stream containing ketones, alkenes and carbon dioxide; and
   d) separating the alkenes from the intermediate product stream yielding an alkene depleted intermediate product stream and the separated alkenes.

2. The method according to claim 1, comprising:
   subjecting the feedstock to prehydrogenation reaction in a presence of hydrogenation catalyst prior to step b).

3. The method according to claim 1, comprising:
   purifying the feedstock prior to step b).

4. The method according to claim 1, comprising,
   purifying the ester of fatty acid and the monohydric alcohol prior to step c).

5. The method according to claim 1, comprising:
subjecting the ester of fatty acid and the monohydric alcohol to prehydrogenation reaction in a presence of hydrogenation catalyst prior to step c).

6. The method according to claim 1, wherein the ketonisation catalyst comprises:
$TiO_2$ as active catalyst material.

7. The method according to claim 1, comprising:
performing the ketonisation reaction of step c) at least partially in liquid phase.

8. The method according to claim 1, wherein the ketonisation reaction of step c) is at a temperature in a range from 100 to 500° C., and at a pressure in a range from atmospheric pressure to 10 MPa, in a presence of a ketonisation catalyst.

9. The method according to claim 1, wherein the ketonisation reaction of step c) is performed in a presence of a $CO_2$ flow of 0.5-1.0 kg $CO_2$/kg ester feed.

10. The method according to claim 1, wherein step c) comprises:
adding a monohydric alcohol having a carbon chain length of two or more to the ketonisation reaction.

11. The method according to claim 1, comprising:
separating the carbon dioxide from the intermediate product stream.

12. A method for producing renewable wax, the method comprising:
producing an alkene depleted intermediate product stream according to claim 1; and
subjecting the alkene depleted intermediate product stream to hydrodeoxygenation reaction to yield renewable wax.

13. A method for producing renewable base oil fulfilling API Group lll base oil specifications having ≥90 wt % saturated hydrocarbons, ≤0.03 wt-% sulfur and a viscosity index of ≥120, the method comprising:
producing an alkene depleted intermediate product stream according to claim 1; and
subjecting the alkene depleted intermediate product stream to both hydrodeoxygenation reaction and to hydroisomerisation reaction, simultaneously or in sequence, to yield a deoxygenated and isomerized product stream containing renewable base oil components.

14. The method according to claim 12, wherein the hydrodeoxygenation reaction is performed at a temperature in a range from 100 to 500° C.; a pressure in a range from atmospheric pressure to 20 MPa; a WHSV in a range from 0.5 to 3 h$^{-1}$, and a $H_2$ flow of 350-900 nl $H_2$/l feed, in a presence of a hydrodeoxygenation catalyst.

15. The method according to claim 13, wherein subjecting to hydrodeoxygenation and to hydroisomerisation is made in sequence, and wherein the method comprises:
separating liquids from gases between hydrodeoxygenation and hydroisomerisation.

16. The method according to claim 13, wherein the hydroisomerisation reaction is performed at a temperature in range from 200 to 450° C.; a pressure in a range from 1 to 15 MPa; a WHSV in a range from 0.5-3 h$^{-1}$, and a $H_2$ flow of 100-800 nl $H_2$/l feed, in a presence of a hydroisomerisation catalyst comprising a Group VIII metal and a molecular sieve, optionally on an alumina and/or silica support.

17. The method according to claim 13, wherein the method comprises:
distilling the deoxygenated and isomerized product stream comprising the renewable base oil to obtain distilled renewable base oil and one or more of liquified petroleum gas, naphtha and diesel/jet fuel.

18. The method according to claim 1, wherein the monohydric alcohol has a carbon chain length from 2 to 20.

19. The method according to claim 1, wherein the monohydric alcohol.

20. The method according to claim 8, wherein the ketonisation reaction of step c) is at a temperature in a range from 300 to 400° C., and at a pressure in a range from atmospheric pressure from 0.5 to 3 MPa, in a presence of a ketonisation catalyst.

21. The method according to claim 12, wherein the hydrodeoxygenation reaction is performed at a temperature in the range from 250 to 400° C.; a pressure in a range from atmospheric pressure from 0.2 to 8 MPa; a WHSV in a range from 0.5 to 3 h$^{-1}$, and a $H_2$ flow of 350-900 nl $H_2$/l feed, in a presence of a hydrodeoxygenation catalyst.

22. The method according to claim 13, wherein the hydroisomerisation reaction is performed at a temperature in a range from 250 to 400° C.; a pressure in a range from 1 to 6 MPa; a WHSV in a range from 0.5-3 h$^{-1}$, and a $H_2$ flow of 100-800 nl $H_2$/l feed, in a presence of a hydroisomerisation catalyst comprising a Group VIII metal and a molecular sieve, optionally on an alumina and/or silica support.

23. The method according to claim 1, wherein the monohydric alcohol has a carbon chain length from 2 to 10.

24. The method according to claim 1, wherein the monohydric alcohol is renewable ethanol.

25. The method according to claim 13, wherein the hydrodeoxygenation reaction is performed at a temperature in a range from 100 to 500° C.; a pressure in a range from atmospheric pressure to 20 MPa; a WHSV in a range from 0.5 to 3 h$^{-1}$, and a H2 flow of 350-900 nl $H_2$/l feed, in a presence of a hydrodeoxygenation catalyst.

26. The method according to claim 25, wherein subjecting to hydrodeoxygenation and to hydroisomerisation is made in sequence, and wherein the method comprises:
separating liquids from gases between hydrodeoxygenation and hydroisomerisation.

27. The method according to claim 26, wherein the hydroisomerisation reaction is performed at a temperature in range from 200 to 450° C.; a pressure in a range from 1 to 15 MPa a WHSV in a range from 0.5-3 h$^{-1}$, and a $H_2$ flow of 100-800 nl $H_2$/l feed, in a presence of a hydroisomerisation catalyst containing a Group VIII metal and a molecular sieve, optionally on an alumina and/or silica support.

* * * * *